(12) United States Patent
Laus et al.

(10) Patent No.: US 7,414,108 B2
(45) Date of Patent: Aug. 19, 2008

(54) COMPOSITION AND METHOD FOR PRODUCING AN IMMUNE RESPONSE AGAINST TUMOR-RELATED ANTIGENS

(75) Inventors: Reiner Laus, Bellevue, WA (US); Curtis L. Ruegg, Redwood City, CA (US); Michael H. Shapero, Redwood City, CA (US); Demao Yang, Mountain View, CA (US)

(73) Assignee: Dendreon Corporation, Seattle, WA (US)

( * ) Notice: Subject to any disclaimer, the term of this patent is extended or adjusted under 35 U.S.C. 154(b) by 300 days.

(21) Appl. No.: 10/772,856

(22) Filed: Feb. 4, 2004

(65) Prior Publication Data

US 2004/0141991 A1    Jul. 22, 2004

Related U.S. Application Data

(63) Continuation of application No. 09/402,845, filed as application No. PCT/US98/07232 on Apr. 10, 1998, now abandoned.

(60) Provisional application No. 60/043,301, filed on Apr. 11, 1997.

(51) Int. Cl.
*C07K 5/10* (2006.01)

(52) U.S. Cl. .......................................... 530/350; 514/2
(58) Field of Classification Search ........................ None
See application file for complete search history.

(56) References Cited

U.S. PATENT DOCUMENTS 5,882,864 A * 3/1999 An et al. ........................ 435/6

OTHER PUBLICATIONS

Roitt et al, (Immunology, 1993, Mosby, St. Louis, p. 6.4-6.5).*
Bost et al. (Immunol. Invest. 1988; 17:577-586).*
Sharief et al (Biochem. Biophys. Res. Commun.) 184:1468-1476(1992), abstract only attached.*
Bork, *Genome Research 10*:398-400, (2000).
Bowie, et al., *Science 247*:1306-1310, (1990).
Burgess, et al., *J Cell Bio 111*:2129-2138, (1990).
Fong, L., et al., *Proc Amer Assoc Cancer Research 88th Annual Meeting 38*:356 #2386 (1997).
Fong, L., et al., *Journal of Immunology 159*:3113-3117 (1997).
Iype, et al., *Arch Biochem Biophys 128*(2):434-441, (1968).
Johnstone, et al., *Immunochemistry in Practice*, 2nd Edition, Blackwell Scientific Publications, Oxford, England, pp. 30, (1987).
Kuciel, et al., *Biotechnol Apl Biochem 10*(3):257-272, (1988).
Lazar, et al., *Molecular and Cellular Biology 9*:1247-1252, (1988).
Marra, M., et al., Database EBML—EMEST12, Entry MM3841, Acc. No. W08384 (1996).
Roiko, K., et al., *Gene 89*:223-229 (1990).
Ruegg, C.L., et al., *FASEB Journal 12*(4)a277 #1614 (1998).
Sharief, et al, *BBRC 184*:1468-1476, (1992).
Zhai, Y., et al., *Journal of Immunotherapy 20*(1):15-25 (1997).

* cited by examiner

*Primary Examiner*—Misook Yu
*Assistant Examiner*—Mark Halvorson
(74) *Attorney, Agent, or Firm*—Susan J. Myers Fitch; Peter J. Dehlinger; King & Spalding LLP

(57) ABSTRACT

Disclosed are a novel prostatic acid phosphatase and corresponding coding region derived from mouse. Also disclosed is a method of producing an immune response against an autologous polypeptide tumor antigen by immunizing a subject with a xenogeneic polypeptide antigen, either alone, as part of a viral antigen construct, or as part of a pulsed dendritic cell preparation.

6 Claims, No Drawings

```
                            SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 1158 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: mouse prostatic acid phosphatase
            (mPAP)

(xi) SEQUENCE DESCRIPTION: SEQ ID NO: 1:

ATGGGAGCCG TTCCTCTGCC CCTGAGCCCG ACAGCAAGCC TCAGCCTTGG CTTCTTGCTC        60

CTGCTTTCTC TCTGCCTGGA CCCAGGCCAA GCCAAGGAGT TGAAGTTTGT GACATTGGTG       120

TTTCGACATG GAGACCGAGG TCCCATCGAG ACCTTTCCTA CCGACCCCAT TACGGAATCC       180

TCGTGGCCAC AAGGATTTGG CCAACTCACC CAGTGGGGCA TGGAACAGCA CTACGAACTT       240

GGAAGTTATA TAAGGAAAAG ATACGGAAGA TTCTTGAACG ACACCTATAA GCATGATCAG       300

ATTTATATCC GGAGCACAGA TGTGGACAGG ACTTTGATGA GTGCTATGAC AAACCTTGCA       360

GCCCTGTTTC CTCCAGAGGG GATCAGCATC TGGAATCCTA GACTGCTCTG GCAGCCCATC       420

CCAGTGCACA CCGTGTCTCT CTCTGAGGAT CGGTTGCTGT ACCTGCCTTT CAGAGACTGC       480

CCTCGTTTTG AAGAACTCAA GAGTGAGACT TTAGAATCTG AGGAATTCTT GAAGAGGCTT       540

CATCCATATA AAGCTTCCT  GGACACCTTG TCGTCGCTGT CGGGATTCGA TGACCAGGAT       600
```

```
CTTTTTGGAA TCTGGAGTAA AGTTTATGAC CCTTTATTCT GCGAGAGTGT TCACAATTTC    660

ACCTTGCCCT CCTGGGCCAC CGAGGACGCC ATGATTAAGT TGAAAGAGCT ATCAGAATTA    720

TCTCTGCTAT CACTTTATGG AATTCACAAG CAGAAAGAGA AATCTCGACT CCAAGGGGGC    780

GTCCTGGTCA ATGAAATCCT CAAGAATATG AAGCTTGCAA CTCAGCCACA GAAGTATAAA    840

AAGCTGGTCA TGTATTCCGC ACACGACACT ACCGTGAGTG GCCTGCAGAT GGCGCTAGAT    900

GTTTATAATG GAGTTCTGCC TCCCTACGCT TCTTGCCACA TGATGGAATT GTACCATGAT    960

AAGGGGGGGC ACTTTGTGGA GATGTACTAT CGGAATGAGA CCCAGAACGA GCCCTACCCA   1020

CTCACGCTGC CAGGCTGCAC CCACAGCTGC CCTCTGGAGA GTTTGCGGA GCTACTGGAC    1080

CCGGTGATCC CBCAGGACTG GGCCACGGAG TGTATGGCCA CAAGCAGCCA CCAAGGTACT   1140

GTGGGCGCTT TGGGTTAG                                                 1158

(2) INFORMATION FOR SEQ ID NO: 2:

(i) SEQUENCE CHARACTERISTICS:
        (A) LENGTH: 385 amino acids
        (B) TYPE: amino acid
        (D) TOPOLOGY: linear (vi) ORIGINAL SOURCE:
        (C) INDIVIDUAL ISOLATE: mouse prostatic acid phosphatase
            (mPAP) coding sequence (xi) SEQUENCE DESCRIPTION: SEQ ID NO: 2:

Met Gly Ala Val Pro Leu Pro Leu Ser Pro Thr Ala Ser Leu Ser Leu
 1               5                  10                  15

Gly Phe Leu Leu Leu Leu Ser Leu Cys Leu Asp Pro Gly Gln Ala Lys
            20                  25                  30

Glu Leu Lys Phe Val Thr Leu Val Phe Arg His Gly Asp Arg Gly Pro
        35                  40                  45

Ile Glu Thr Phe Pro Thr Asp Pro Ile Thr Glu Ser Ser Trp Pro Gln
50                  55                  60

Gly Phe Gly Gln Leu Thr Gln Trp Gly Met Glu Gln His Tyr Glu Leu
65                  70                  75                  80

Gly Ser Tyr Ile Arg Lys Arg Tyr Gly Arg Phe Leu Asn Asp Thr Tyr
                85                  90                  95

Lys His Asp Gln Ile Tyr Ile Arg Ser Thr Asp Val Asp Arg Thr Leu
            100                 105                 110

Met Ser Ala Met Thr Asn Leu Ala Ala Leu Phe Pro Pro Glu Gly Ile
        115                 120                 125

Ser Ile Trp Asn Pro Arg Leu Leu Trp Gln Pro Ile Pro Val His Thr
130                 135                 140

Val Ser Leu Ser Glu Asp Arg Leu Leu Tyr Leu Pro Phe Arg Asp Cys
145                 150                 155                 160

Pro Arg Phe Glu Glu Leu Lys Ser Glu Thr Leu Glu Ser Glu Glu Phe
                165                 170                 175

Leu Lys Arg Leu His Pro Tyr Lys Ser Phe Leu Asp Thr Leu Ser Ser
            180                 185                 190

Leu Ser Gly Phe Asp Asp Gln Asp Leu Phe Gly Ile Trp Ser Lys Val
        195                 200                 205

Tyr Asp Pro Leu Phe Cys Glu Ser Val His Asn Phe Thr Leu Pro Ser
210                 215                 220

Trp Ala Thr Glu Asp Ala Met Ile Lys Leu Lys Glu Leu Ser Glu Leu
225                 230                 235                 240
```

```
Ser Leu Leu Ser Leu Tyr Gly Ile His Lys Gln Lys Glu Lys Ser Arg
                245                 250                 255

Leu Gln Gly Gly Val Leu Val Asn Glu Ile Leu Lys Asn Met Lys Leu
            260                 265                 270

Ala Thr Gln Pro Gln Lys Tyr Lys Lys Leu Val Met Tyr Ser Ala His
        275                 280                 285

Asp Thr Thr Val Ser Gly Leu Gln Met Ala Leu Asp Val Tyr Asn Gly
    290                 295                 300

Val Leu Pro Pro Tyr Ala Ser Cys His Met Met Glu Leu Tyr His Asp
305                 310                 315                 320

Lys Gly Gly His Phe Val Glu Met Tyr Tyr Arg Asn Glu Thr Gln Asn
                325                 330                 335

Glu Pro Tyr Pro Leu Thr Leu Pro Gly Cys Thr His Ser Cys Pro Leu
            340                 345                 350

Glu Lys Phe Ala Glu Leu Leu Asp Pro Val Ile Pro Gln Asp Trp Ala
        355                 360                 365

Thr Glu Cys Met Ala Thr Ser Ser His Gln Gly Thr Val Gly Ala Leu
    370                 375                 380

Gly
385

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (vi) ORIGINAL SOURCE:
        (C) INDIVIDUAL ISOLATE: gene specific primer for 5' end
            cloning of mPAP from mouse prostate (first round)

(xi) SEQUENCE DESCRIPTION: SEQ ID NO: 3:

CATTCCGGTA GTACATCTCC AC                                              22

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (vi) ORIGINAL SOURCE:
        (C) INDIVIDUAL ISOLATE: gene specific primer for 5' end
            cloning of mPAP from mouse prostate (second round)

(xi) SEQUENCE DESCRIPTION: SEQ ID NO: 4:

GTCACAAACT TCAACTCCTT GG                                              22

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vi) ORIGINAL SOURCE:
        (C) INDIVIDUAL ISOLATE: gene specific primer for 3' end
            cloning of mPAP from mouse prostate (first round)

(xi) SEQUENCE DESCRIPTION: SEQ ID NO: 5:
```

```
GATGTACTAC CGGAATGAGA C                                              21

(2) INFORMATION FOR SEQ ID NO: 6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (vi) ORIGINAL SOURCE:
        (C) INDIVIDUAL ISOLATE: gene specific primer for 3' end
            cloning of mPAP from mouse prostate (second round)

(ix) FEATURE:
        (A) NAME/KEY: Other
        (B) LOCATION: 1, 10
        (D) OTHER INFORMATION:   ote: "where N is A, G, C, or T"

(xi) SEQUENCE DESCRIPTION: SEQ ID NO: 6:

NGTGATCCCN CARGACTGG                                                 19

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (vi) ORIGINAL SOURCE:
        (C) INDIVIDUAL ISOLATE: synthetic anchor primer one (AP1) for
            mPAP cloning (xi) SEQUENCE DESCRIPTION: SEQ ID NO: 7:

CCATCCTAAT ACGACTCACT ATAGGGC                                        27

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vi) ORIGINAL SOURCE:
        (C) INDIVIDUAL ISOLATE: synthetic anchor primer two (AP2) for
            mPAP cloning (xi) SEQUENCE DESCRIPTION: SEQ ID NO: 8:

ACTCACTATA GGGCTCGAGC GGC                                            23

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (vi) ORIGINAL SOURCE:
        (C) INDIVIDUAL ISOLATE: forward primer (A31091) for mPAP
            amplification (xi) SEQUENCE DESCRIPTION: SEQ ID NO: 9:

AAGTGCAGCA CCTCCTAAGG                                                20

(2) INFORMATION FOR SEQ ID NO: 10:

(i) SEQUENCE CHARACTERISTICS:
```

```
        (A) LENGTH: 19 base pairs
        (B) TYPE: nucleic acid
        (C) STRANDEDNESS: single
        (D) TOPOLOGY: linear (vi) ORIGINAL SOURCE:
        (C) INDIVIDUAL ISOLATE: reverse primer (A31093) for mPAP
            amplification (xi) SEQUENCE DESCRIPTION: SEQ ID NO: 10:

GCACTTCCTG CTGAGCTCC                                                    19

(2) INFORMATION FOR SEQ ID NO: 11:

(i) SEQUENCE CHARACTERISTICS:
        (A) LENGTH: 31 amino acids
        (B) TYPE: amino acid
        (D) TOPOLOGY: linear (vi) ORIGINAL SOURCE:
        (C) INDIVIDUAL ISOLATE: signal peptide of the deduced amino
            acid sequence for mPAP (xi) SEQUENCE DESCRIPTION: SEQ ID NO: 11:

Met Gly Ala Val Pro Leu Pro Leu Ser Pro Thr Ala Ser Leu Ser Leu
 1               5                  10                  15

Gly Phe Leu Leu Leu Leu Ser Leu Cys Leu Asp Pro Gly Gln Ala
            20                  25                  30
```

COMPOSITION AND METHOD FOR PRODUCING AN IMMUNE RESPONSE AGAINST TUMOR-RELATED ANTIGENS

This application is a continuation of U.S. application Ser. No. 09/402,845 filed Mar. 14, 2000, now abandoned; which is a 35 USC §371 application of International Application No. PCT/US98/07232 filed Apr. 10, 1998, designating the United States; which claims priority to U.S. Provisional Application No. 60/043,301 filed Apr. 11, 1997, now abandoned, all of which are hereby incorporated by reference in their entirety.

FIELD OF THE INVENTION

The invention relates to immunotherapeutic compositions and methods for producing immunity against tumor-related antigens. Such compositions and methods are useful in reducing tumor cell load.

REFERENCES

Ausubel, F. M., et al., *CURRENT PROTOCOLS IN MOLECULAR BIOLOGY*, John Wiley and Sons, Inc., Media Pa. (1992).

Mackett, M., et al., *J. Virol.* 49:857-864 (1984).

Sambrook, et al., *MOLECULAR CLONING: A LABORATORY MANUAL* (Second Edition), Cold Spring Harbor Press, Plainview, N.Y. (1989).

BACKGROUND OF THE INVENTION

Tumor antigens are generally proteins or glycoproteins that are present on the surface of tumor cells. In many cases, such antigens are identical to or highly similar to antigens that are present on normal, non-tumor cells in the host organism, allowing the tumor cells to escape the host's immunological surveillance mechanisms.

Traditional means of reducing tumor load in afflicted individuals have relied on chemical or radiation treatments that target particular attributes of tumor cell growth, such as hormone dependence, rate of growth, and the like. Such treatments have been shown to be effective in combatting certain types of tumors, but relatively or incompletely effective in other cases. Therefore, methods to enhance or augment the ability of an organism to immunologically eradicate some or all circulating tumor cells (tumor load) are needed.

For example, in the case of prostate tumors, although the five-year survival rates for localized prostate cancer have improved significantly, the prognosis for metastatic forms of the disease has not been improved in recent years. Prostectomy (simple or radical) and local radiation therapy are effective at early stages of the disease, but are of little or no benefit in the later, metastatic stages of the disease. Moreover, metastatic forms of prostate cancer are generally resistant to conventional anti-neoplastic chemotherapy.

The only therapy that has shown benefit so far in the disseminated form of the disease is androgen ablation, either by castration or estrogen (diethylstilbestrol) therapy. Prostate tumor cells are typically dependent on testosterone or other androgens as growth factors. However, androgen withdrawal frequently leads to outgrowth of androgen-independent, mutant tumor cells. Thus, since all currently available therapies for disseminated prostate cancer are at best palliative and do not prolong survival, improved therapies for eradicating circulating or disseminated prostate tumor cells are needed.

The present invention is concerned with an immunotherapeutic treatment method that takes advantage of the observation that is the discovery of the invention, that is, animals immunized with xenogeneic antigens can be made to mount an immune response against closely related self-antigens, such as the antigens present on tumor cells. Such a therapy has the advantages over conventional therapies that (i) it mobilizes the body's natural mechanisms for ridding itself of the diseased cells, (ii) it can be directed to disseminated forms of the disease, and (iii) it can be used to either augment or replace conventional anti-tumor therapy.

SUMMARY OF THE INVENTION

The present invention provides novel compositions and methods for producing immune responses directed against tumor-related antigens. More specifically, the invention includes a novel tumor-related antigen, mouse prostatic acid phosphatase (mPAP) which can be used as a xenogeneic antigen to induce prostate-directed immunity in other mammalian species. The invention further includes several novel vehicles which can be used to carry out immunization with xenogeneic prostatic acid phosphatase (PAP) that leads to therapeutic immunity directed against other forms of PAP tumor antigen, including human PAP. These vehicles include viruses, such as vaccinia virus, or dendritic cells which express mPAP, human PAP or rat PAP. Further, the present invention includes the discovery that immunization with xenogeneic forms of recombinant PAP protein leads to formation of cross-reactive antibodies which react with the autologous form of PAP.

In a related embodiment, the invention includes the discovery of a novel prostatic acid phosphatase (PAP) polypeptide isolated from mouse, which is xenogeneic with respect to human PAP, and which can therefore be used as an antigen to produce a humoral and/or cellular response against tumor antigens resident in a subject, according to the methods described herein. The isolated PAP polypeptide has at least about 90%, and preferably at least 95% sequence identity to the sequence presented as SEQ ID NO: 2 (mPAP). It is further appreciated that the PAP antigen can be formed by substituting amino acids that represent conservative substitutions for the amino acids of the polypeptide sequence identified as SEQ ID NO: 2, according to the teachings presented herein.

The invention also includes polynucleotides that encode the PAP polypeptides described above. In a preferred embodiment, the polynucleotide has the sequence presented as SEQ ID NO: 1. In addition, the invention includes vectors, such as baculoviral vectors, that carry such polynucleotides, along with appropriate regulatory elements effective for expression of the polynucleotide in the host.

As mentioned above, the invention also includes a method of inducing an immune response against a tumor-associated antigen in a mammalian subject by administering to the subject an immunogenic dosage of a composition which includes a xenogeneic form of the tumor-related antigen from a different mammalian species.

In one particular embodiment, the tumor associated antigen is human prostatic acid phosphatase, and the administered xenogeneic antigen is a non-human PAP. In a more specific embodiment, the xenogeneic antigen includes mouse PAP, as described above. Such an antigen composition may be produced in any of a number of expression systems known in the art; in a particular described embodiment it is produced in insect cells.

In an alternative embodiment, the antigen composition may be a recombinant virus which expresses the xenogeneic antigen. In preferred embodiments, the recombinant virus is vaccinia, adeno, or adeno-like virus, and the xenogeneic antigen is a non-human PAP, such as mouse PAP, as described above. In still another preferred embodiment, the xenogeneic antigen composition includes a dendritic cell pulsed in vitro with a xenogeneic antigen, which may be, in a further preferred embodiment, a non-human PAP, such as mouse PAP.

In a related aspect, the invention includes an immunogenic composition for eliciting an immune response against a tumor-related antigen in a mammalian species. The composition includes a recombinant vaccinia virus that expresses a xenogeneic form of a tumor-related antigen. In a preferred embodiment the xenogeneic form of the tumor-related antigen is a non-human PAP, such as the mouse PAP polypeptide forms discussed above.

In still another related aspect, the invention includes an immunogenic composition for eliciting a cellular immune response against a tumor-related antigen in a mammalian species. In this embodiment, the composition includes a dendritic cell that has been pulsed in vitro with a xenogeneic form of the tumor-related antigen. In a preferred form, the xenogeneic form of the tumor-related antigen includes a non-human PAP, such as mouse PAP, as discussed above.

These and other objects and features of the invention will become more fully apparent when the following detailed description of the invention is read in conjunction with the accompanying drawings.

BRIEF DESCRIPTION OF THE SEQUENCES

SEQ ID NO: 1 is a nucleotide sequence for mouse prostatic acid phosphatase (mPAP);

SEQ ID NO: 2 is a deduced amino acid sequence for mPAP;

SEQ ID NO: 3 is a gene specific primer used for cloning the 5' end of mPAP from mouse prostate (first round);

SEQ ID NO: 4 is a gene specific primer used for cloning the 5' end of mPAP from mouse prostate (second round);

SEQ ID NO: 5 is a gene specific primer used for cloning the 3' end of mPAP from mouse prostate (first round);

SEQ ID NO: 6 is a gene specific primer used for cloning the 3' end of mPAP from mouse prostate (second round);

SEQ ID NO: 7 is synthetic anchor primer one (AP1) used in cloning mPAP;

SEQ ID NO: 8 is synthetic anchor primer two (AP2) used in cloning mPAP;

SEQ ID NO: 9 is the forward primer (A31091) of a pair of primers used to amplify mPAP;

SEQ ID NO: 10 is the reverse primer (A31093) of a pair of primers used to amplify mPAP; and SEQ ID NO: 11 is the signal sequence present in SEQ ID NO: 2.

DETAILED DESCRIPTION OF THE INVENTION

I. Definitions

Unless otherwise indicated, all terms used herein have the same meaning as they would to one skilled in the art of the present invention. Practitioners are particularly directed to Sambrook, et al. (1989) and Ausubel, et al., for definitions and terms of the art. It is to be understood that this invention is not limited to the particular methodology, protocols, and reagents described, as these may vary.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

The term "vector" refers to a nucleotide sequence that can assimilate new nucleic acids, and propagate such new sequences in an appropriate host. Vectors include, but are not limited to recombinant plasmids and viruses. The vector (e.g., plasmid or recombinant virus) comprising the nucleic acid of the invention can be in a carrier, for example, a plasmid complexed to protein, a plasmid complexed with lipid-based nucleic acid transduction systems, or other non-viral carrier systems. The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

The term "splice variant" refers to a polypeptide that is coded by a common gene but which has a sequence that is altered due to alternative splicing of the mRNA prior to translation. Such splicing may result in a deletion of or addition of one or more amino acids (peptide segments) at any point in the polypeptide.

When referred to in the context of an mRNA transcript, a "splice variant" is an mRNAs produced by alternative splicing of coding regions, i.e., exons, from the common gene.

Amino acid residues are referred to herein by their standard single- or three-letter notations: A, ala, alanine; C, cys, cysteine; D, asp, aspartic acid; E, glu, glutamic acid; F, phe, phenylalanine; G, gly, glycine; H, his, histidine; I, ile, isoleucine; K, lys, lysine; L, leu, leucine; M, met, methionine; N, asn, asparagine; P, pro, proline; Q, gln, glutamine; R, arg, arginine; S, ser, serine; T, thr, threonine; V, val, valine; W, trp, tryptophan; X, hyp, hydroxyproline; Y, tyr, tyrosine.

A "conservative substitution" refers to the substitution of an amino acid in one class by an amino acid in the same class, where a class is defined by common physicochemical amino acid sidechain properties and high substitution frequencies in homologous proteins found in nature (as determined, e.g., by a standard Dayhoff frequency exchange matrix or BLOSUM matrix). Six general classes of amino acid sidechains, categorized as described above, include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

The term "immunogenic dosage" as used herein refers to a dosage of antigen that, when administered to a suitable vertebrate subject, produces a detectable immune response, such a humoral response (circulating antibodies) or a cellular response (antigen-specific T-lymphocytes). This response may develop in days or weeks, depending on the dosage, the species or strain of animal immunized, and the immunization schedule employed by the researcher. Such variables and their assessment are known in the art; further, methods of extrapolating data from experimental animals, such as mice or rats, to humans is also known in the art.

The term "xenogeneic", as used herein, refers to a polypeptide antigen that is derived from a species other than the reference species, where such foreign species' antigen exhibits substantial identity—e.g., at least 60-95%, and preferably at least 70-95% sequence identity—to the reference species' antigen. In this context, the term "substantial identity" refers to concordance of an amino acid sequence with another amino acid sequence or of a polynucleotide sequence with another polynucleotide sequence when such sequences are arranged in a best fit alignment in any of a number of sequence alignment proteins known in the art.

A "xenogeneic form of an antigen" refers to an antigen having substantial sequence identity to a reference antigen, but derived from a different species of animal.

The term "autologous", as used herein, refers to polypeptide antigens derived from the same species as the reference species.

II. Immunogenic Compositions

A. Tumor-Associated Antigens

The rationale for using tumor-associated antigens in cancer therapy is based on the observation that several tumor antigen-specific immune effector mechanisms can be utilized to attack tumors. Both cellular and humoral immune responses may contribute to tumor rejection in a variety of experimental and clinical models. Passively applied antibodies have shown promise in diseases such as B-cell lymphoma. However, this treatment requires identification and cloning of a specific individual's tumor antigen. Further, since tumor antigens are generally autoantigens (e.g., self-antigens to which the individual is tolerant) it has been difficult to achieve an effective or reliable immune response, using immunological approaches. Conventional adjuvants may not be sufficient to break established tolerance towards autoantigens.

By way of example, in prostate cancer, the two best-studied tumor markers are prostatic acid phosphatase (PAP) and prostate-specific antigen (PSA). More recently, a prostate-specific membrane antigen (PSM) has been cloned that was originally identified by the monoclonal antibody 7E11.C5.

Currently, the most widely used tumor marker in prostate cancer is prostate-specific antigen (PSA). PSA displays an exquisite specificity and sensitivity for detecting and monitoring prostate cancer. It is a member of the glandular kallikrein family and as such displays substantial sequence homology to other members of this gene family. More specifically, human glandular kallikrein and pancreatic/renal kallikrein share 78% and 57% of their respective amino acid sequence with PSA.

An alternative antigen that combines the features of well-established tissue specificity and relative uniqueness of amino acid sequence is prostatic acid phosphatase (PAP). PAP is the prostate-specific isoenzyme of the heterogeneous group of acid phosphatases. Physiologically, it occurs as a homodimer with a molecular weight of approximately 102 kD. PAP is a secreted enzyme of unknown physiological significance. It occurs in concentrations of approximately 1 mg/ml in seminal plasma. Elevated serum levels of PAP caused by PAP-secreting tumor cells is found in 33%, 79%, 71% and 92% of patients with stages A, B, C and D prostatic cancer, respectively. Elevation of prostatic acid phosphatase in patients with stage D prostate cancer was noted to be associated with significantly shortened survival, while decreased levels of serum acid phosphatase correlated with response to therapy. Studies with PAP-specific monoclonal antibodies and RNA probes indicate that the PAP antigen is strictly prostate-specific.

Immunohistochemical studies reveal that PAP is expressed by the normal prostate and >90% of adenocarcinomas of the prostate, but is not expressed by other tissues. Since PAP is expressed by the healthy prostate, it has been difficult to elicit an immune response to human PAP using human PAP as an antigen.

It is the discovery of the present invention that xenogeneic tumor-associated antigens can be used to elicit an immune response to the autologous, tumor-associated antigen. For example, and as exemplified below, prostatic acid phosphatases (PAPs) derived from human and rat share 78% sequence identity; PAPs from human and mouse share 80% sequence identity; and PAPs from rat and mouse share 87% sequence identity. Thus, within the context and definitions of the present invention, mouse PAP is xenogeneic with respect to humans, and vice-versa.

Data presented herein (See Section III, below), show that immunization of a rodent using autologous PAP as immunogen stimulates antibodies (humoral response) that react with self antigen. However, such autologous immunization did not result in a cellular immune response as would be needed to combat tumor cells in vivo. In contrast, as shown below, in accordance with the discovery of the present invention, when the xenogeneic antigen was used as antigen, production of both a humoral and a cellular response were elicited.

B. Prostatic Acid Phosphatase Antigen Compositions

The cDNA for human and rat PAP have been isolated. In humans, a 3061 bp-cDNA contains an open reading frame of 1158 bp that codes for a protein 386 amino acids (aa) in length. After cleavage of a 32 aa signal peptide a 41 kD peptide backbone is generated. Three N-glycosylation sites occur on each chain.

The mouse form of PAP has not been previously described. In experiments carried out in support of the present invention, mouse PAP has been cloned and its nucleotide and deduced amino acid sequences identified. Example 1 provides details of the cloning procedures used to isolate the mouse polynucleotide sequence, shown as SEQ ID NO: 1. Using this sequence, the deduced polypeptide sequence was determined (SEQ ID NO: 2).

The N-terminal 31 amino acid portion of the polypeptide sequence shown as SEQ ID NO: 2 represents the predicted signal peptide and is referred to herein as SEQ ID NO: 11. The polypeptide composition of the invention includes the mouse PAP identified herein as SEQ ID NO: 2, including minor, conservative substitutions therein, where such substitutions preserve the biological activity of the protein and do not alter the sequence by more than 10%, or preferably 5%. Conservative substitutions are well known in the art. It is further appreciated that mPAP may retain its identity and utility as a xenogeneic antigen when it has at least 90% and preferably 95% identity to SEQ ID NO: 2.

Six general classes of amino acid sidechains, categorized as described above, include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). A substitution of one member of a single class for another member of the same class represents a conservative substitution, in accordance with the present invention. For example, substitution of an Asp for another class III residue such as Asn, Gln, or Glu, is a conservative substitution.

As mentioned above and described in further detail below, it has been found that the mouse PAP antigen is effective to serve as an immunogen capable of eliciting a cellular immune response against human PAP. Accordingly, it is appreciated that this novel polypeptide has utility as an anti-tumor immunogen. The polynucleotide coding sequence and vectors containing this sequence therefore have utility in the manufacture of the polypeptide immunogen by recombinant means. Such polynucleotides and vectors can be constructed according to methods well known in the art (Ausubel, et al., 1992). In the context of the present invention, the mouse PAP coding sequence includes SEQ ID NO: 1 and any minor modifications thereof, including but not limited to equivalent codons and codon modifications made to conform with codon preferences of a particular expression vector and/or organism. As discussed above, the invention also includes its expression product, SEQ ID NO: 2, as well as splice variants thereof.

Selection of particular vectors for use with specific cell types will be within the skill of persons skilled in the art of recombinant protein expression.

For example, insect cells and the lytic baculovirus *Autographa californica* nuclear polyhidrosis virus (AcNPV) can be used as an expression system for production of the polypeptide compositions of the invention. This system is particularly desirable, because it is capable of providing a glycosylated product. Production of mouse and rat PAP in insect cells is detailed in Example 1. Other suitable expressions systems, including appropriate promoters and expression vectors, will be known to those skilled in the art, and include, but are not limited to adeno virus, adeno-like virus and the like.

III. Compositions and Methods for Inducing an Immune Response

It is the discovery of the present invention that a xenogeneic antigen can be used to induce an immune response against a closely related autologous tumor antigen. Methods and dosages for producing humoral and/or cellular responses are exemplified in the methods illustrated in the sections that follow, including the referenced examples. In general, the practitioner will appreciate that an immunogenic dosage can be determined empirically and/or extrapolated from appropriate experimental species. Empirical determinations are made by administering small initial doses (the equivalent of an approximately 200-500 μg dose of xenogeneic antigen composition in rat, or about $10^7$ cells producing recombinant peptide, as described below) according to methods known in the art and measuring for a detectable immune response, such a humoral response (circulating antibodies) or a cellular response (antigen-specific T-lymphocytes), according to methods well known in the art or exemplified below. Such a response may develop in days or weeks, depending on the dosage, the species or strain of animal immunized, and the immunization schedule employed by the researcher. Such variables and their assessment are known in the art; further, methods of extrapolating data from experimental animals, such as mice or rats, to humans is also known in the art.

A. Xenogeneic Antigen Immunogens

Xenogeneic antigens of the present invention can be used to induce humoral and/or cellular responses, according to the methods described below. Example 3 provides details of methods used to induce a xenogeneic humoral response in rats. TABLE 1 shows humoral responses of rats immunized with human PAP, which is xenogeneic with respect to rat. As shown, antibodies that recognized both the foreign, xenogeneic antigen (human PAP) and the autologous polypeptide (rat PAP) were detected. As a control, rats immunized with a control polypeptide (ovalbumin) did not produce antibodies that reacted with either the immunizing antigen or the autologous PAP.

TABLE 1

| Immunization | Test Antigen | | |
|---|---|---|---|
| (Strain/Immunogen) | Ovalbumin | rat PAP | human PAP |
| COP rats/human PAP | 0 | + | + |
| COP rats/ovalbumin | + | 0 | 0 |
| WISTAR rats/human PAP | 0 | + | + |
| WISTAR rats/ovalbumin | + | 0 | 0 |

Similarly, as shown in TABLE 2, when mice were immunized with either rat, human or mouse PAP, in each case, antibodies were detected that reacted with all three of the antigens. This further shows that immunization with xenogeneic antigen elicits a response against the reference, self-antigen, in this case, mouse PAP.

TABLE 2

| Immunization | Test Antigen | | | |
|---|---|---|---|---|
| (Strain/Immunogen) | Ovalbumin | rat PAP | mouse PAP | human PAP |
| C57/b16 mice/human PAP | 0 | + | + | + |
| C57/b16 mice/rat PAP | 0 | + | + | + |
| C57/b16 mice/mouse PAP | 0 | + | + | + |
| C57/b16 mice/ovalbumin | + | 0 | 0 | 0 |

These data show that the rodent forms of PAP are capable of inducing an anti-human PAP immune response thus, they are suitable for inducing prostate-cancer directed immunity in patients who suffer from PAP-positive tumors.

B. Vaccinia Virus PAP Immunogens

Example 3 provides details of experiments carried out in support of the present invention in which xenogeneic PAP was tested for its ability to also induce cellular immunity that cross-reacts with autologous PAP. Recombinant vaccinia viruses were constructed to express rat PAP or human PAP. These viruses were then used to immunize rats, i.e., a xenogeneic immunization. Cellular immunity towards autologous PAP was measured by detecting infiltration by immune cells of PAP-expressing organs, producing, for example, the response known as "autoimmune prostatitis." RatPAP and humanPAP as described in Example 2 were processed to produce recombinant vaccinia viruses essentially as described by Mackett, et al. (1984) which reference is incorporated herein by reference. Autoimmune damage (prostatitis) caused by these immunizations was detected after routine histopathology examination of prostates. Histopathological findings in vaccinia-immunized rats are summarized in TABLE 3, where "0" indicates no change, "(+)" indicates a mild response, and "+++" indicates a robust cellular response.

TABLE 3

| Immunogen | Autoimmune Damage to the Prostate[1] |
|---|---|
| 0 | 0 |
| wild-type vaccinia virus | (+) |
| vaccinia virus-ratPAP | (+) |
| vaccinia virus-humanPAP | +++ |

[1](Scale: 0-4)

As demonstrated by these experiments, the vaccinia virus-human PAP construct (e.g., a xenogeneic antigen construct) was particularly effective in eliciting a cellular immune response against rat PAP in vivo. Surprisingly, it was more effective in raising such a response than was the corresponding ratPAP-vaccinia virus construct. From these experiments it is anticipated that a rodent protein, such as rat PAP or mouse PAP will be effective as an immunogen that is capable of stimulating a cellular immune response against autologous (human PAP) tumor antigen. The implications of this type of response in the context of anti-tumor therapy are appreciated by the present invention. It is further appreciated that such response can be produced by any of a number of appropriate viral expression systems, including, but not limited to, vaccinia, adeno and adeno-like viruses.

C. Pulsed Dendritic Cells

In a related aspect, the invention includes immunogenic compositions comprising dendritic cells pulsed in vitro with a xenogeneic tumor antigen, as discussed above.

In practice, dendritic cells are isolated from an individual, using known methods, one of which is described in Example 5, herein. The dendritic cells are mixed with a xenogeneic antigen of interest, such as mouse PAP or ratPAP, using standard methods, such as the general methods described in Example 6. The cell preparation may then be depleted of $CD4^+$ T-cells by solid phase immunoadsorption and further fractionated to enrich for cells having cytolytic activity. Doses of about $10^6$ to $10^9$, and preferably, about $10^7$ cells are then administered to the subject by intravenous or central injection according to established procedures (e.g., infusion over 30 to 60 minutes). The responsiveness of the subject to this treatment is measured by monitoring the induction of a cytolytic T-cell response, a helper T-cell response and antibody response towards the tumor-related antigen of interest in peripheral blood mononuclear cells by methods well known in the art. Alternatively, autoimmune damage can be measured as described for PAP in part B, above.

In addition to the direct in vivo administration regimen described above, the xenogeneic antigen-pulsed dendritic cells can be used, for example, in ex vivo somatic therapy, in vivo implantable devices and ex vivo extracorporeal devices. They can also be employed in the screening of antigenicity and immunogenicity of peptide epitopes from tumor- and virus-specific antigens.

The following examples illustrate, but in no way are intended to limit the present invention.

EXAMPLES

Example 1

Molecular Cloning of Mouse PAP

Mouse prostatic acid phosphatase (mPAP) was cloned in the polymerase chain reaction (PCR) using primers derived from the known ratPAP sequence and synthetic anchor primers that were attached to the 5' and 3' ends of the cDNA respectively. Rat sequences that could cross-prime the unknown mouse sequence were determined experimentally by evaluating multiple primers empirically.

mPAP was cloned from mouse prostate organ as follows: Poly A+ RNA was prepared from whole mouse prostates. cDNA was synthesized using the Marathon RACE System (Clontech, Palo Alto, Calif.) and the 3' RACE System (Gibco BRL; Gaithersburg, Md.) according to instructions provided by the manufacturer. The 5' end of the cDNA was cloned as a 5' RACE product from mouse prostate Marathon cDNA by subjecting it to 2 rounds of PCR using the following primers in each round:

1st Round: synthetic anchor primer 1 (AP1) and gene-specific primer 5-CATTCCGGTAGTACATCTCCAC-3 (SEQ ID NO: 3)

2nd Round: AP1 and gene specific primer 5-GTCA-CAAACTTCAACTCCTTGG-3 (SEQ ID NO: 4)

The 3' end of the cDNA was cloned as a 3' RACE product from mouse prostate Marathon cDNA by subjecting it to 2 rounds of PCR using the following primers in each round:

1st Round: synthetic anchor primer 1 (AP1) and gene-specific primer 5-GATGTACTACCGGAATGAGAC-3 (SEQ ID NO: 5)

2nd Round: synthetic anchor primer 2 (AP2) and gene-specific primer 5-NGTGATCCCNCARGACTGG-3 (SEQ ID NO: 6)

```
AP1 : 5-CCATCCTAATACGACTCAACTAT    (SEQ ID NO: 7)
AGGGC-3

AP2 : 5-ACTCACTATAGGGCTCGAGCGGC-3  (SEQ ID NO: 8)
```

In the foregoing sequences, R is A or G, and N is A,G,C or T/U.

Specific RACE products were subcloned and DNA sequence was obtained by DNA sequencing with a Fluorescence-based automated sequencer (ABI 373A, Perkin-Elmer/Applied Biosystems). PCR primers were designed according to this partial sequence information to amplify the full-length mouse Pap cDNA using standard PCR conditions.

The following primer pair was used:

```
A31091 (f) : 5-AAGTGCAGCACCTCC      (SEQ ID NO: 9)
TAAGG-3

A31093 (r) : 5-GCACTTCCTGCTGAG      (SEQ ID NO: 10)
CTCC-3
```

The cDNA obtained in this way was subcloned and both strands were sequenced using standard methods on the ABI 373A sequencer. The cDNA included a 1158 base pair open reading frame (SEQ ID NO: 1) which codes for a 385 amino acid polypeptide (SEQ ID NO: 2), including a signal peptide as the first 31 residues (SEQ ID NO: 11).

Example 2

Expression of mPAP and ratPAP in Insect Cells

The cDNA encoding mPAP, rat PAP and human were cloned into the pBacPAK8 baculovirus recombination vector (Clontech). rPAP cDNA was amplified from first strand cDNA made from mRNA isolated from rat prostate (Harlan) using primers which delineate the fragment containing nucleotides 15-1177 (Genbank Acc. M32397) and add an exogenous Xho I restriction site at the 5'-end and exogenous BamHI and Bln I sites at the 3'-end to facilitate insertion into the pBacPAK8 vector. mPAP was obtained as described in example 1. Both cDNAs were modified by inclusion of a synthetic polynucleotide sequence at the 3' end which codes for six histidine residues (HIS6). This tag was used for purification of recombinant PAPs with metal-chelate affinity chromatography. The cDNA encoding human PAP was amplified by PCR from first strand cDNA made from mRNA isolated from the human prostate carcinoma cell line LNCaP (ATCC CRL 1740) using primers which delineate the fragment containing nucleotides 1-1175 (Genbank Acc. M34840) and add an exogenous Xho I restriction site at the 5'-end and exogenous BamHI and Xba I sites at the 3'-end to facilitate insertion into the pBacPAK8 BV recombination vector (Clontech). This Xba I site is engineered to provide an in-frame stop codon for human PAP.

Recombinant Baculovirus.

The PAP plasmids were each mixed with linearized BV viral genome plasmid and the mixtures were each transfected into Sf21 cells using Lipofectin as supplied in a recombinant BV transfection kit (Clontech). Six days after transfection, the culture supernatants were collected and titrated on Sf21 monolayers under agarose to form viral plaques. Four days later the cells were stained with neutral red and candidate viral plaques were picked and expanded on Sf21 cells to screen for recombinant BV using PAP enzymatic activity as a readout. PAP+ BV clones were chosen and expanded in Sf21 large-scale suspension cultures for viral stocks and subsequently for protein production using protein-free Sf900 II media (Gibco/BRL).

All recombinant proteins exhibited PAP enzymatic activity as shown by hydrolysis of PNPP in a standard acid phosphatase assay. They were purified to >80% purity by affinity chromatography on nickel-charged columns (Qiagen) according to instructions which were provided by the manufacturer.

Example 3

Immunization with Xenogeneic Antigen

Purified recombinant mPAP and rPAP were used to immunize rats (COP and WISTAR inbred strains) or mice (C57/b16). Rats were immunized with 200 μg protein in complete Freund's adjuvant subcutaneously. They received booster immunizations on days 14 and 28. Antibody responses were measured on day 42. Mice were immunized in a similar fashion except that 500 μg or 100 μg of recombinant protein were used in each immunization. Control groups of animals were immunized with ovalbumin in doses and adjuvant equivalent to the PAP immunizations.

Antibody titers of immune animals were determined with standard solid phase ELISA assays which were performed by coating purified PAP onto ELISA plates. Plates were then reacted with test sera. Bound antibodies were detected with horseradish-peroxidase (HRP)-coupled Goat-anti rat (or anti-mouse) antibodies respectively.

Example 4

Vaccinia Viral Construct PAP Antigens

Xenogeneic immunity was compared to cellular immunity that cross-reacts with autologous PAP. Therefore, we constructed recombinant vaccinia viruses that express rat PAP or human PAP. These viruses were used to immunize rats cellular immunity towards autologous PAP can be measured by detecting infiltration by immune cells of PAP-expressing organs, i.e., autoimmune prostatitis. RatPAP and humanPAP as described in example 3 were processed to produce recombinant vaccinia viruses essentially as described by Mackett, et al. (1984). The recombinant viruses were grown in COS-7 cells (ATCC) and were used to immunize male COP rats. Autoimmune damage caused by these immunizations was detected after routine histopathology examination of prostates. Histopathological findings in vaccinia-immunized rats are summarized in Table 3.

Example 5

Preparation of Dendritic Cells

Buffy coats prepared from one unit of blood from HLA-A0201 positive volunteer healthy donors are obtained from the Stanford University Blood Center (Stanford, Calif.). Cells are harvested from the leukopacs, diluted to 60 mL using Ca++/Mg++ free phosphate buffered saline (D-PBS; Gibco Laboratories, Grand Island, N.Y.) and layered over two 15 mL columns of organosilanized colloidal silica (OCS) separation medium (prepared as described by Dorn in U.S. Pat. No. 4,927,749, incorporated herein by reference, at a density 1.0720 gr/ml, pH 7.4, 280 mOsm/kg H₂O) in 50 mL centrifuge tubes, preferably cell-trap tubes. The OCS medium is preferably prepared by reacting and thus blocking the silanol groups of colloidal silica (approx. 10-20 nm diameter particles) with an alkyl trimethoxy silane reagent and has the structural formula:

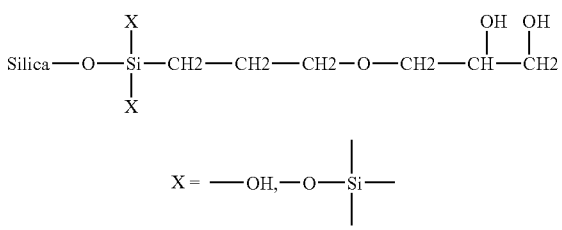

Related colloidal silicas and methods for production thereof are disclosed in U.S. Pat. No. 4,927,749 to Dorn. In a preferred embodiment, the OCS density gradient material is diluted to an appropriate specific density in a physiological salt solution supplemented with polyvinylpyrrolidone (PVP) such as PVP-10 available from Sigma Chemical Co. (St. Louis, Mo.).

The tubes are centrifuged at 1000×g for 35 minutes at room temperature. The centrifuge run is allowed to stop without braking and the peripheral blood mononuclear cells (PBMC), present at the interface, are harvested.

PBMC are resuspended in D-PBS, centrifuged once at 650×g for 10 minutes and twice more at 200×g for 5 minutes to remove platelets. Platelet-depleted PBMC are resuspended in 60 mL of D-PBS, layered on top of two columns of 15 mL of OCS (density 1.0610 gr/ml, 280 mOsm/kg H₂O) in a centrifuge tube and centrifuged at 650×g for 25 minutes at 4° C. without braking. The resulting interface (primarily monocytes) and pellet cells (primarily lymphocytes) are harvested and washed with D-PBS by centrifugation at room temperature (once at 650×g for 10 minutes and twice thereafter at 200×g for 5 minutes).

In instances where the dendritic cells are used to generate peptide-specific cytotoxic T lymphocytes (CTL) for purposes of elucidating their antigen presentation function, the interface fraction (mostly monocytes) is resuspended in cold pooled human AB serum (Irvine Scientific, Santa Ana, Calif.) to which an equal volume of 80% AB serum 20% dimethyl sulfoxide (DMSO) (Sigma Chemical Company, St. Louis, Mo.) is added dropwise. The resulting cell suspension is aliquoted into cryovials and frozen in liquid nitrogen. The monocytes can be used for restimulation of CTL for expansion.

The pellet fraction is resuspended in 100 mL of AB Culture Medium, inoculated into two T-75 tissue culture flasks and cultured in a humidified 5% CO₂ incubator for 40 hours. Following the incubation, the non adherent cells are harvested by moderate pipeting, washed and resuspended at a concentration of 2-5×10⁶ cells/mL in AB Culture Medium. The cell suspension is overlayered over four columns of 4.0 mL OCS separation medium (density 1.0565 gr/ml, pH 7.4, 280 mOsm/kg H₂O), in AB Culture Medium and centrifuged at 650×g for 20 minutes at room temperature without braking.

The interface and pellet cells are harvested and washed in AB Culture Medium (Basal RPMI-1640 medium, Gibco Laboratories, Grand Island, N.Y.) by centrifugation once at 650×g for 10 minutes and twice thereafter at 200×g for 5 minutes each at room temperature. The yield and viability of both cell fractions is estimated by counting on a hemocytometer using trypan blue exclusion.

The purity of dendritic cells in the interface fraction is quantified following analysis on a flow cytometer (FACS). Dendritic cells are characterized as negative for cell phenotype markers CD3 (T lymphocytes), CD14 (monocytes), CD16 (NK cells) and CD20 (B-cells) and positive for HLA class 11 expression using dual staining with HLA-DR (on the FITC channel) and a cocktail of CD3, CD 14, CD16, CD20 (on the PE channel). Dual staining with IgG2a on both the FITC and PE channels can be used as isotype control.

The morphology of the cells can also be evaluated using photomicroscopy. The DC enriched fraction contains large sized veiled cells with cytoplasmic processes extending from the cell surface, features characteristic of DC.

Example 6

Induction of Prostate Tumor Antigen-Specific CTL by Xenogeneic PAP

A T-cell in vitro priming and expansion system is used to establish the utility of xenogeneic PAP in the generation of HLA class I restricted CTL, a cellular immune response.

HLA-A2.1-positive PBMNC are isolated by standard methods on density gradient (FICOLL-HYPAQUE, Pharmacia Fine Chemicals, Piscataway, N.J.) having a density of 1.077 gr/ml. The cells are primed with mouse PAP at a concentration of about 10 µg/ml for two or five days. The cell preparation is then depleted of CD4+ T-cells by solid phase immunoadsorption and separated into low density and high density cells over a 1.068 gr/ml density gradient. The different fractions are then cultured separately in AIM V media (Gibco, Gaithersberg, Md.) supplemented with rIL-2 (20 U/ml). Autologous PBMNC that are cultured in Aim V media are used as antigen presenting cells (dendritic cells) for restimulation at weekly intervals. Lytic potential of the cells can be assessed in a standard 4-hour chromium release assay with the HLA-A2-1-transgenic prostate carcinoma cell line LnCaP.FGC as a target. This cell line is described in co-owned PCT application published as WO97/24438, incorporated herein by reference in its entirety.

To investigate whether the observed cytotoxicity is a HLA-class I-restricted CD8+ cytolytic T-cell mediated phenomenon a blocking assay with the monomorphic HLA class I-specific monoclonal antibody W6/32 (ATCC) antibody can be performed. W6/32 blocks HLA class I mediated killing in standard assays, whilst control antibody CA141 is specific for HLA class II (DR) and will not interfere with class I restricted killing.

While the invention has been described with reference to specific methods and embodiments, it will be appreciated that various modifications and changes may be made without departing from the invention.

The invention claimed is:

1. An isolated polypeptide that induces an immune response to human prostatic acid phosphatase, wherein the isolated polypeptide comprises a sequence having at least 95% amino acid sequence identity to the sequence identified by SEQ ID NO:2.

2. The isolated polypeptide of claim 1, wherein the polypeptide has the sequence of SEQ ID NO:2.

3. A method of inducing an immune response against human prostatic acid phosphatase (PAP) in a mammalian subject, comprising administering to the subject an immunogenic dosage of a composition comprising an isolated polypeptide of claim 1.

4. The method of claim 3, wherein the isolated polypeptide is mouse PAP.

5. The method of claim 3, wherein the isolated polypeptide has the amino acid sequence of SEQ ID NO:2.

6. The method of claim 3, wherein the isolated polypeptide is produced in insect cells.

* * * * *